United States Patent [19]

Devas

[11] 4,059,102
[45] Nov. 22, 1977

[54] BONE SECURING DEVICES

[75] Inventor: Michael Bertrand Devas, Bexhill-on-Sea, England

[73] Assignee: National Research Development Corporation, London, England

[21] Appl. No.: 727,995

[22] Filed: Sept. 30, 1976

Related U.S. Application Data

[63] Continuation of Ser. No. 599,074, July 25, 1975, abandoned.

[30] Foreign Application Priority Data

Aug. 1, 1974 United Kingdom ............... 34014/74

[51] Int. Cl.² ............................................... A61F 5/04
[52] U.S. Cl. ................................................. 128/92 B
[58] Field of Search ............ 128/92 B, 92 BA, 92 BB, 128/92 BC, 92 R, 83

[56] References Cited

U.S. PATENT DOCUMENTS

| 2,270,188 | 1/1942 | Longfellow | 128/92 BA |
| 2,489,870 | 11/1949 | Dzus | 128/92 B |
| 2,952,254 | 9/1960 | Keating | 128/92 BB |
| 3,716,051 | 2/1973 | Fischer | 128/92 BB |
| 3,875,936 | 4/1975 | Volz | 128/92 B X |

FOREIGN PATENT DOCUMENTS 1,159,049  7/1969  United Kingdom ............... 85/42

Primary Examiner—John D. Yasko
Attorney, Agent, or Firm—Cushman, Darby & Cushman

[57] ABSTRACT

A bone screw is provided having leading and trailing end portions with respective threads of opposite hands. The leading end portion will normally be narrower than the trailing end portion, and either or both portions can be tapered towards their leading ends.

2 Claims, 6 Drawing Figures

BONE SECURING DEVICES

This application is a continuation of my copending application Ser. No. 599,074, filed July 25, 1975, which was abandoned when this application was accorded its filing date.

This invention concerns bone securing devices and more particularly bone screws such as used for fracture fixation, usually in association with bone plates and other endoprosthetic devices.

Apart from specific differences which may arise from a choice of particular material to suit the environment in which the screws are to be used, or choice of particular threads to suit the mechanical properties of bone, currently available bone screws are not essentially different in form and function from other screws.

As such, a bone screw is conventional in its inability to connect together two non-rotatable component parts, be they fractured bone parts or one such part and an ancillary device, such that the screw itself threadably engages with both parts and at the same time exerts a compressive force between the parts. This compound function only arises when one of the component parts rotates in the manner of a nut, but bone screws are normally used in a situation where the component parts are to be retained in predetermined dispositions.

However, this is not to say that the relevant compound function would not be useful. On the contrary, threaded engagement with a component part is normally desirable to enhance securement and distribute load, while compression between component parts enhances bone union after fracture fixation. Accordingly, any possibility of achieving both functions from a bone screw is clearly useful in various situations.

An object of the present invention is to realize this possibility and to this end the invention provides a bone screw having a first thread of one hand extending from one end of the screw over a leading longitudinal portion thereof, and second thread of opposite hand extending over a trailing longitudinal portion of the screw.

In the use of such a screw, the same is screwed by use of the second thread into and through a first component part to be engaged thereby, towards the second such component, this action positioning the trailing end of the screw within the first component part. Then this screw action is reversed to engage the leading end of the screw with the second component part by way of the first thread. Thus both component parts are threadably engaged with the screw, and the two component parts are drawn together under compression both by the screwing action into the second component part and the unscrewing action in the first component part.

In so far as the trailing end of the screw passes into a component part during use, there normally will be no enlarged head at the trailing end. Correspondingly, in so far as the leading end portion passes through the site to be engaged by the trailing end portion, the former normally will be of smaller diameter than the latter.

Also, since either of the leading and trailing end portions can be used to cut a thread in a component part, typically when this is bone, or to mesh with a correspondingly threaded part, typically when this is a bone plate or similar device, either of these portions of the screw can be tapered towards its leading end.

For a clearer and fuller understanding of the present invention, the same will now be described by way of example with reference to the accompanying drawings, in which.

Figure 1:
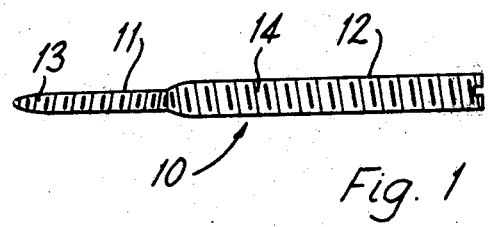
FIG. 1 illustrates one embodiment of the present invention.
Figure 5:
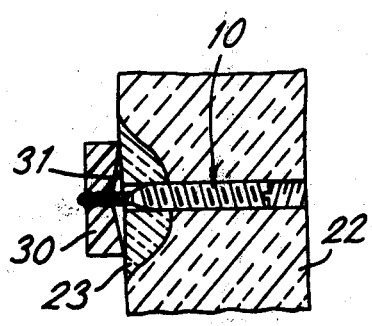
Figure 6:
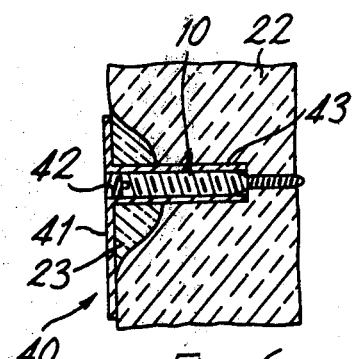

FIGS. 5 and 6 respectively illustrate further uses of the embodiment of FIG. 1 in association with different ancillary devices.

The bone screw of FIG. 1 is denoted generally at 10, and has a leading end portion 11 and a trailing end portion 12 respectively formed with first and second threads 13 and 14 of opposite hand. Each of the portions 11 and 12 is of nominally cylindrical form with a convergent tapering towards its leading end, the portion 12 being of larger diameter than portion 11, and portion 12 being formed with a screw-driver engageable slot 15 at its trailing end.

Figure 2:
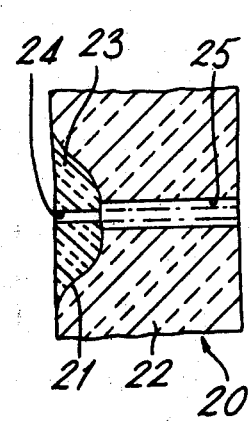
FIGS. 2 to 4 illustrate one use of the embodiment of FIG. 1.
Figure 3:
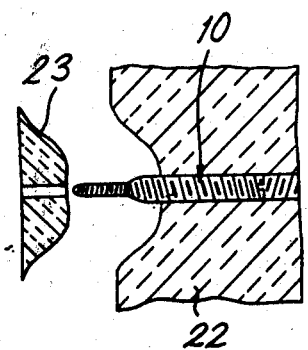
Figure 4:
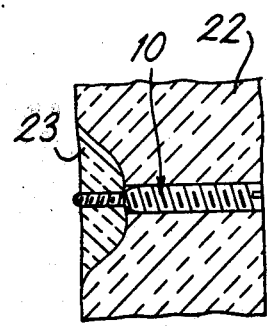

One mode of use of the screw of FIG. 1 is illustrated by FIGS. 2 to 4 which show a bone 20 fractured at 21 into two component parts 22 and 23.

FIG. 2 shows the bone 20 drilled to provide a pilot bore 24 which passes successively through the component parts 22 and 23 when correctly mutually located, with part 23 then being counterbored to provide an enlarged bore 25.

FIG. 3 shows the part 23 separated from part 22, and the screw 20 screwed into the part 22, towards part 23, by use of the thread 14. In this connection, it is to be noted that the counterboring of part 22 provides a bore 25 which serves as a pilot bore relative to screw portion 12 with its thread 14, while serving as an effective clearance bore for screw portion 11 with its opposite thread 13. Also, it will be noted that this first screw action is continued until the trailing end of the screw is located within the bone part 22, with the leading end portion 11 of the screw projecting into the space normally occupied by the bone part 23.

FIG. 4 illustrates the result of a second screw action, whereby the pilot bore 24 in bone part 23 is applied to the screw leading end and the screw then rescrewed in the opposite sense to that of the first screw action. This reversed screw action screws the leading end portion 11 into bone part 23 by use of the thread 13 and, at the same time, withdraws the trailing end portion 12 by use of its thread 14 relative to bone part 22. In the result, bone part 23 is drawn rapidly towards bone part 22 and these parts held together under compression, while each part is threadably engaged by the screw. Moreover, it is to be noted that an appropriate choice of dimensions for the screw allows the same to be wholly located within the confines of the bone.

This mode of use is particularly useful for fracture fixation in a situation where a relatively small fragment of bone is to be united with a main body of bone in the region of a joint. However, the screw of FIG. 1 is not limited to such a use, but can find other applications. One example of an alternative use is illustrated by FIG. 5.

In FIG. 5 the screw 10 is used in a similar situation to that of FIG. 2, but in association with an ancillary device 30 in the form of a resilient disc or plate of plastics material such as high density polyethylene having one face 31 concavely dished. In this case, the device 30 effectively serves the role of bone part 23 relative to the screw and is provided with the pilot bore 25, while the bone part 23 is formed with an extension of bore 25. Thus, in FIG. 5, the screw trailing end portion is first engaged with bone part 22 as before, and the leading end is passed through bone part 23 to screw into the device 30 by the subsequent reverse action, the device being located with its concave face adjacent the bone. In the result, the screw is engaged with the bone part 22 and the device 30, while the bone part 23 is held therebetween under compression in appropriate location with part 22.

The use of a plastics material and dishing for device 30 is advantageous in readily affording resilience to allow enhanced compression without damage of the bone by the device, and in allowing a self-tapping action by the screw with resultant economy in production of the device.

As to circumstances of use in which a device such as 30 is appropriate: these include situations in which the mechanical quality of the bone is inadequate to afford sound screw securement except within a relatively extensive body of such bone.

FIG. 6 illustrates a further example of use of the screw 10 in association with a different form of ancillary device denoted generally at 40. The device 40 serves the role of a bone plate which usually takes the form of a rigid strip apertured for passage of bone screws therethrough. In this case, device 40 includes such a strip 41 with at least one of the apertures 42 being extended from one side of the strip by a tube 43 which is internally threaded to co-operate with the thread 14 of the screw 10.

FIG. 6 shows the device 40 located with its strip 41 alongside the bone 20 with the tube 43 received in the bone part 22, and the screw to extend through the device and bone with its threads 13 and 14 respectively engaged with bone part 23 and tube 22. This situation is similar to that of FIG. 5, but with the relevant ancillary devices co-operating with opposite ends of the screw, and the procedure of use will be evident from the earlier discussion.

While the proposed screw has been described with more particular reference to the illustrated embodiment having a variety of uses, the screw itself can equally be varied. For example, when used with an ancillary device, such as 40 in FIG. 6, which is threaded to co-operate with the screw, the relevant screw portion clearly need not be tapered. Moreover this is relevant to either the leading or trailing portion of the screw since both portions can co-operate with such a device. Also, it is not essential that the trailing portion of the screw have a larger diameter than the leading portion, since both portions can co-operate with respective threaded ancillary devices in a single reverse screwing action to withdraw into one at the trailing end and advance into the other at the leading end.

I claim:

1. A new use for a screw of the type which has a leading end portion with a thread of one hand therearound and a trailing end portion with a thread of opposite hand therearound, said new use being to connect together two mutually nonrotatable component parts, each of which is one of a fragment of a fractured bone and a fracture fixation device for disposition against said bone and said new use comprising the method of:

screwing one of said end portions of said screw into one of said component parts, and then screwing the other of said screw end portions into the other of said component parts while partially unscrewing said screw from said one component part to locate said screw through said bone and to effect compressive force on said bone between said component parts.

2. The use according to claim 1 wherein said leading end portion is of lesser diameter than said trailing end portion, said one component part is provided with a bore which is a clearance fit for said leading end portion but not for said trailing end portion, said screw is applied with said leading end portion foremost to said bore, said trailing end portion is screwed into said bore to project said leading end portion from the remote end of said bore, and said leading end portion is thereafter screwed into said other component part.

* * * * *